United States Patent
Pazenok et al.

(10) Patent No.: US 9,856,222 B2
(45) Date of Patent: Jan. 2, 2018

(54) PROCESS FOR PREPARING 3,5-BIS(HALOALKYL)PYRAZOLE DERIVATIVES VIA ACYLATION OF HYDRAZONES

(71) Applicant: Bayer CropScience Aktiengesellschaft, Monheim am Rhein (DE)

(72) Inventors: Sergii Pazenok, Solingen (DE); Norbert Lui, Odenthal (DE)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 0 days.

(21) Appl. No.: 15/317,921

(22) PCT Filed: Jun. 8, 2015

(86) PCT No.: PCT/EP2015/062691
§ 371 (c)(1),
(2) Date: Dec. 9, 2016

(87) PCT Pub. No.: WO2015/189141
PCT Pub. Date: Dec. 17, 2015

(65) Prior Publication Data
US 2017/0107182 A1    Apr. 20, 2017

(30) Foreign Application Priority Data
Jun. 11, 2014 (EP) .................... 14172037

(51) Int. Cl.
*C07D 231/12* (2006.01)
(52) U.S. Cl.
CPC .................. *C07D 231/12* (2013.01)
(58) Field of Classification Search
None
See application file for complete search history.

(56) References Cited

U.S. PATENT DOCUMENTS 6,706,911 B1    3/2004   Lui et al.

FOREIGN PATENT DOCUMENTS

| WO | WO-03518200 | 6/2003 |
|----|----|----|
| WO | WO-03070705 | 8/2003 |
| WO | WO-2005042468 | 5/2005 |
| WO | WO 2008013925 | 1/2008 |
| WO | WO-2008022777 | 2/2008 |
| WO | WO-2009106230 | 9/2009 |
| WO | WO-2009112157 | 9/2009 |
| WO | WO-2012025557 | 3/2012 |
| WO | WO-2013113829 | 8/2013 |
| WO | WO-2014033164 | 6/2014 |

OTHER PUBLICATIONS

Extended European Search Report dated Aug. 29, 2014 for European Application No. 14172037.5 filed on Jun. 11, 2014, 5 pages.
International Search Report dated Jul. 16, 2015 for PCT Application No. PCT/EP2015/062691 filed on Jun. 8, 2015, 10 pages.
Pashkevich et al. (1981). "Fluoroalkyl containing mono- and bispyrazoles", *Zhurnal Vsesoyuznogo Khimicheskogo Obshchestva im. D. I. Mendeleeva* 26(1):105-107, XP009179740. (English translation included).

*Primary Examiner* — Kamal Saeed
(74) *Attorney, Agent, or Firm* — Morrison & Foerster LLP

(57) ABSTRACT

Process for preparing 3,5-bis(haloalkyl)pyrazole derivatives of the formula (I), via acylation of Hydrazones.

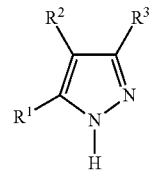

(I)

5 Claims, No Drawings

PROCESS FOR PREPARING 3,5-BIS(HALOALKYL)PYRAZOLE DERIVATIVES VIA ACYLATION OF HYDRAZONES

CROSS REFERENCE TO RELATED APPLICATIONS

This application is the national stage of International Application No. PCT/EP2015/062691, filed internationally on Jun. 8, 2015, which claims the benefit of European Application No. 14172037.5, filed Jun. 11, 2014, the disclosures of which are hereby incorporated by reference in their entireties for all purposes.

The present invention relates to a novel process for preparing 3,5-bis(haloalkyl)pyrazole derivatives.

Polyfluoroalkylpyrazolylcarboxylic acid derivatives and 3,5-bis(haloalkyl)pyrazoles are valuable precursors of active fungicidal ingredients (WO 2003/070705, WO 2008/013925, WO 2012/025557).

Pyrazolecarboxylic acid derivatives are typically prepared by reacting acrylic acid derivatives having two leaving groups with hydrazines (WO 2009/112157 and WO 2009/106230). WO 2005/042468 discloses a process for preparing 2-dihaloacyl-3-aminoacrylic esters by reacting acid halides with dialkylaminoacrylic esters and subsequent cyclization thereof with alkyl hydrazines. WO 2008/022777 describes a process for preparing 3-dihalomethylpyrazole-4-carboxylic acid derivatives by reacting α,α-difluoroamines in the presence of Lewis acids with acrylic acid derivatives and subsequent reaction thereof with alkylhydrazines.

3,5-Bis(fluoroalkyl)pyrazoles are prepared by reacting bisperfluoroalkyl diketones (e.g. 1,1,1,5,5,5-hexafluoroacetylacetone) with hydrazines (cf. Pashkevich et al., Zhurnal Vsesoyuznogo Khimicheskogo Obshchestva im. D. I. Mendeleeva (1981), 26(1), 105-7), the yield being only 27-40%. The synthesis, isolation and purification of the polyfluoroalkyl diketones is very complex since the compounds are generally very volatile and highly toxic.

In the light of the prior art described above, it is an object of the present invention to provide a process that does not have the aforementioned disadvantages and hence gives a route to 3,5-bis(haloalkyl)pyrazole derivatives in high yields.

The object described above was achieved by a process for preparing 3,5-bis(haloalkyl)pyrazoles of the formula (I),

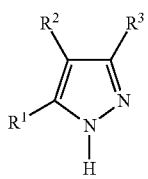

(I)

in which
- $R^1$ and $R^3$ are each independently selected from $C_1$-$C_6$-haloalkyl;
- $R^2$ is selected from H, halogen, COOH, (C=O)$OR^5$, CN and (C=O)$NR^6R^7$;
- $R^5$ is selected from $C_{1-12}$-alkyl, $C_{3-8}$-cycloalkyl, $C_{6-18}$-aryl, $C_{7-19}$-arylalkyl and $C_{7-19}$-alkylaryl;
- $R^6$ and $R^7$ are each independently selected from $C_{1-12}$-alkyl, $C_{3-8}$-cycloalkyl, $C_{6-18}$-aryl, $C_{7-19}$-arylalkyl and $C_{7-19}$-alkylaryl, or where
- $R^6$ and $R^7$ together with the nitrogen atom to which they are bonded may form a four-, five- or six-membered ring characterized in that in step (A), acid derivatives of the formula (II),

(II)

in which
- $R^1$ is as defined above;
- X is selected from F, Cl, Br or —OC(O)$R^1$ are reacted with compounds of the formula (III),

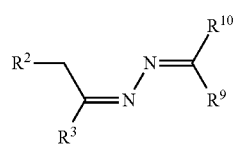

(III)

in which
- $R^9$, $R^{10}$ are each independently selected from $C_{1-12}$-alkyl, $C_{3-8}$-cycloalkyl, $C_{6-18}$-aryl, $C_{7-19}$-arylalkyl, $C_{7-19}$-alkylaryl;
- $R^2$ and $R^3$ are as defined above;

to form the compound of formula (IV):

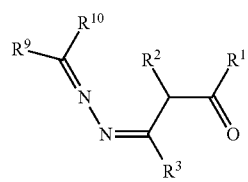

(IV)

in which
- $R^1$, $R^2$, $R^3$, $R^5$, $R^6$, $R^7$, $R^9$, $R^{10}$ are as defined above and that in step (B) cyclization of (IV) takes place to form (I).

Preferred is a process according to the invention, where the radicals in formula (I), (II), (III) and (IV) are defined as follows:
- $R^1$ and $R^3$ are each independently selected from difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-difluoroethyl, 2,2-dichloro-2-fluoroethyl, 2,2,2-trichloroethyl, tetrafluoroethyl ($CF_3CFH$), pentafluoroethyl and 1,1,1-trifluoroprop-2-yl;
- $R^2$ is selected from H, F, Cl, Br, COOCH$_3$, COOC$_2$H$_5$, COOC$_3$H$_7$, CN and CON(CH$_3$)$_2$, CON(C$_2$H$_5$)$_2$;
- $R^9$ is selected from methyl, ethyl, n-, iso-propyl, n-, iso-, sec- and t-butyl, cyclopropyl, cyclobutyl, cyclopentyl, cyclohexyl, phenyl, benzyl, phenylethyl, tolyl, 2,3-, 2,4-, 2,5-, 2,6-, 3,4- or 3,5-dimethylphenyl;
- X is independently selected from F, Cl or —OC(O)$R^1$;
- $R^{10}$ is selected from $C_{1-12}$-alkyl, $C_{3-8}$-cycloalkyl, $C_{7-19}$-arylalkyl.

More preferred is a process according to the invention, where the radicals in formula (I), (II), (III) and (IV) are defined as follows:

$R^1$ and $R^3$ are each independently selected from trifluoromethyl, difluoromethyl, difluorochloromethyl, pentafluoroethyl;

$R^2$ is selected from H, Cl, CN, COO$(C_2H_5)_2$;

$R^9$ is selected from methyl, ethyl, n-, iso-propyl, n-, iso-, sec- and t-butyl, cyclopropyl, cyclobutyl, cyclopentyl, cyclohexyl, benzyl;

X is independently selected from F, Cl or —OC(O)$R^1$;

$R^{10}$ is selected from $C_{1-12}$-alkyl, $C_{3-8}$-cycloalkyl.

Even more preferred is a process according to the invention, where the radicals in formula (I), (II), (III) and (IV) are defined as follows:

$R^1$ and $R^3$ are each independently selected from $CF_2H$, $CF_3$;

$R^2$ is selected from H or $COOC_2H_5$;

$R^9$ is selected from ethyl, n-, iso-propyl, n-, cyclopentyl, cyclohexyl, benzyl;

X is F or —OC(O)$R^1$;

$R^{10}$ is selected from methyl, ethyl, n-, iso-propyl, n-, iso-, sec- and t-butyl.

Most preferred is a process according to the invention, where the radicals in formula (I), (II), (III) and (IV) are defined as follows:

$R^1$ and $R^3$ are each independently selected from $CF_2H$, $CF_3$;

$R^2$ is H;

X is F or —OC(O)$R^1$;

$R^9$ is selected from iso-propyl, benzyl;

$R^{10}$ is selected from methyl, ethyl.

Surprisingly, the pyrazoles of the formula (I) can be prepared under the inventive conditions with good yields and in high purity, which means that the process according to the invention overcomes the abovementioned disadvantages of the preparation processes previously described in the prior art.

General Definitions

In the context of the present invention, the term "halogen" (Hal), unless defined differently, comprises those elements which are selected from the group comprising fluorine, chlorine, bromine and iodine, preferably fluorine, chlorine and bromine, more preferably fluorine and chlorine.

Optionally substituted groups may be mono- or polysubstituted, where the substituents in the case of polysubstitutions may be the same or different.

Haloalkyl: straight-chain or branched alkyl groups having 1 to 6 and preferably 1 to 3 carbon atoms (as specified above), where some or all of the hydrogen atoms in these groups may be replaced by halogen atoms as specified above, for example (but not limited to) $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloro ethyl, 1-bromoethyl, 1-fluoroethyl, 2-fluoroethyl, 2,2-difluoroethyl, 2,2,2-trifluoroethyl, 2-chloro-2-fluoroethyl, 2-chloro,2-difluoroethyl, 2,2-dichloro-2-fluoroethyl, 2,2,2-trichloroethyl, pentafluoroethyl and 1,1,1-trifluoroprop-2-yl. This definition also applies to haloalkyl as part of a composite substituent, for example haloalkylaminoalkyl etc., unless defined elsewhere. Preference is given to alkyl groups substituted by one or more halogen atoms, for example trifluoromethyl ($CF_3$), difluoromethyl ($CHF_2$), $CF_3CH_2$, $CF_2Cl$ or $CF_3CCl_2$.

Alkyl groups in the context of the present invention, unless defined differently, are linear or branched saturated hydrocarbyl groups. The definition $C_1$-$C_{12}$-alkyl encompasses the widest range defined herein for an alkyl group. Specifically, this definition encompasses, for example, the meanings of methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl or n-dodecyl.

Cycloalkyl: monocyclic, saturated hydrocarbyl groups having 3 to 8 and preferably 3 to 6 carbon ring members, for example (but not limited to) cyclopropyl, cyclopentyl and cyclohexyl. This definition also applies to cycloalkyl as part of a composite substituent, for example cycloalkylalkyl etc., unless defined elsewhere.

Aryl groups in the context of the present invention, unless defined differently, are aromatic hydrocarbyl groups which may have one, two or more heteroatoms selected from O, N, P and S. The definition $C_{6-18}$-aryl encompasses the widest range defined herein for an aryl group having 5 to 18 skeleton atoms, where the carbon atoms may be exchanged for heteroatoms. Specifically, this definition encompasses, for example, the meanings of phenyl, cycloheptatrienyl, cyclooctatetraenyl, naphthyl and anthracenyl; 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3 -yl, 1,2,4-thiadiazol-5-yl, 1,2,4 -triazol-3 -yl, 1,3,4 -oxadiazol-2-yl, 1,3,4-thiadiazol-2-yl and 1,3,4-triazol-2-yl; 1-pyrrolyl, 1-pyrazolyl, 1,2,4-triazol-1-yl, 1-imidazolyl, 1,2,3-triazol-1-yl, 1,3,4-triazol-1-yl; 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Arylalkyl groups (aralkyl groups) in the context of the present invention, unless defined differently, are alkyl groups which are substituted by aryl groups, may have one $C_{1-8}$-alkylene chain and may have, in the aryl skeleton, one or more heteroatoms selected from O, N, P and S. The definition $C_{7-19}$-aralkyl group encompasses the widest range defined herein for an arylalkyl group having a total of 7 to 19 atoms in the skeleton and alkylene chain. Specifically, this definition encompasses, for example, the meanings of benzyl and phenylethyl.

Alkylaryl groups (alkaryl groups) in the context of the present invention, unless defined differently, are aryl groups which are substituted by alkyl groups, may have one $C_{1-8}$-alkylene chain and may have, in the aryl skeleton, one or more heteroatoms selected from O, N, P and S. The definition $C_{7-19}$-alkylaryl group encompasses the widest range defined herein for an alkylaryl group having a total of 7 to 19 atoms in the skeleton and alkylene chain. Specifically, this definition encompasses, for example, the meanings of tolyl or 2,3-, 2,4-, 2,5-, 2,6-, 3,4- or 3,5-dimethylphenyl.

The term intermediate used in the context of the present invention describes the substances which occur in the process according to the invention and are prepared for further chemical processing and are consumed or used therein in order to be converted to another substance. The intermediates can often be isolated and intermediately stored or are used without prior isolation in the subsequent reaction step. The term "intermediate" also encompasses the generally unstable and short-lived intermediates which occur transiently in multistage reactions (staged reactions) and to which local minima in the energy profile of the reaction can be assigned.

The inventive compounds may be present as mixtures of any different isomeric forms possible, especially of stereoisomers, for example E and Z isomers, threo and erythro isomers, and optical isomers, but if appropriate also of tautomers. Both the E and the Z isomers are disclosed and claimed, as are the threo and erythro isomers, and also the optical isomers, any mixtures of these isomers, and also the possible tautomeric forms.

Process Description

The process is illustrated in Scheme 1:

Scheme 1:

Step A:

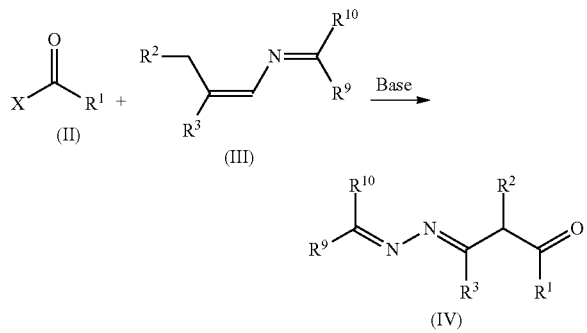

Step B:

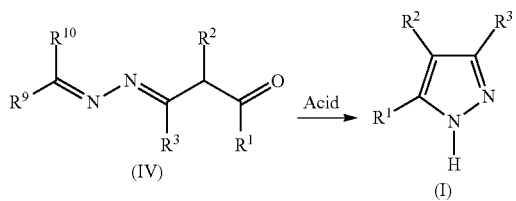

Step A:

In step A, Acid derivatives of the formula (II) are first reacted, in the presence of a base, with compounds of the formula (III).

Preferred compounds of the general formula (II) are Trifluoracetylchloride, Trifluoracetylfluoriede, Difluoracetylfluoride, Difluoroacetylchloride, Trifluorocetylbromide. It is also possible to generate compound of formula (II) in situ for instance using Trfufluoroacetic acid, pivaloyl chloride and pyridine (see WO 2003/051820).

Step A according to the invention is effected at temperatures of 0° C. to +120° C., preferably at temperatures of +20° C. to +100° C., more preferably at 20° C. to +60° C. and under standard pressure. Typical bases are trialkylamines, pyridine, alkylpyridines, picolines, DBU. Preferred bases are alkylpyridines.

The reaction time is not critical and may, according to the batch size and temperature, be selected within a range between a few minutes and several hours.

For the process according to the invention 1 to 2 mol, preferably 1 to 1.5 mol, most preferably 1 to 1.2 mol of the acid derivatives of the formula (II) is reacted with 1 mol of compounds of formula (III).

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane. Particular preference is given, for example, to THF, acetonitriles, ethers, toluene, xylene, chlorobenzene, n-hexane, cyclohexane or methylcyclohexane, and very particular preference, for example, Dichloromethane, ether or dichloromethane. The intermediates of the formula (V) formed can be used in the cyclization step without prior workup.

Alternatively, the intermediates can be isolated by suitable workup steps, characterized and optionally further purified.

Compounds of formula (III) can be prepared from aldehydes or ketones of formula (V) according to the scheme shown below:

Scheme 2:

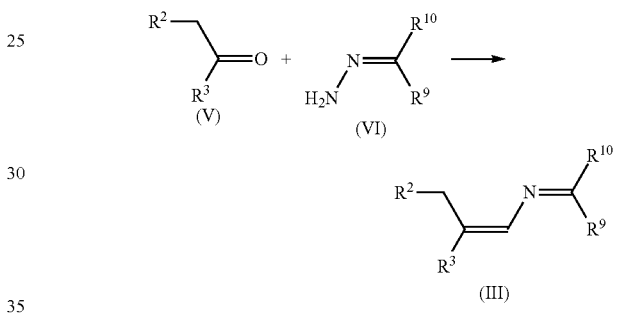

The reaction of compounds of formula (V) (in which the radicals are as defined above) and compounds of formula (VI) (in which the radicals are as defined above) is effected at temperatures of −40° C. to +120° C., preferably at temperatures of +20° C. to +100° C., more preferably at 20° C. to +60° C. and under standard pressure.

For this process 0.9 to 1.8 mol, preferably 1 to 1.6 mol, most preferably 1 to 1.4 mol of the compound of the formula (V) is reacted with 1 mol of the compound of the formula (VI).

It is preferred to have a ratio of 1:1.

The reaction time is not critical and may, according to the batch size and temperature, be selected within a range between a few and many hours. The typical reaction time is 1-5 h.

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane, alcohols such as methanol, ethanol, isopropanolm butanol. Particular preference is given, for example, to THF, acetonitriles, ethers, toluene, xylene, chlorobenzene, n-hexane, cyclohexane or methylcyclohexane, ethanol and very particular preference, for example, to acetonitrile, THF, ether, dichloromethane, ethanol.

Step B:

The cyclization in step (B) of the compound of formula (IV) is effected at temperatures of −40° C. to +80° C., preferably at temperatures of +20° C. to +70° C., more preferably at +60° C. and under standard pressure.

The reaction time is not critical and may, according to the batch size, be selected within a relatively wide range.

Typically, the cyclization step (B) is effected without changing the solvent.

Typically the cyclization of compound of the formula (IV) proceeds under acidic condition.

Preference is given to mineral acids, for example $H_2SO_4$, HCl, HF, HBr, HI, $H_3PO_4$ or organic acids, for example $CH_3COOH$, $CF_3COOH$, p-toluenesulphonic acid, methanesulphonic acid, trifluoromethanesulphonic acid. 0.1 mol to 2 mol, preferably 0.1 to 1.5 mol of the acid for 1 mol of the compound of formula (IV) is used.

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; alcohols such as methanol, ethanol, isopropanol or butanol, nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane. Particular preference is given, for example, to acetonitrilestoluene, xylene, chlorobenzene, n-hexane, cyclohexane or methylcyclohexane, and very particular preference, for example, to acetonitriles, THF, toluene or xylene. After the reaction has ended, for example, the solvents are removed and the product is isolated by filtration, or the product is first washed with water and extracted, the organic phase is removed and the solvent is removed under reduced pressure.

The compounds of the formula (I) where $R^2$ equals (C=O)$OR^5$ can then be converted to pyrazole acids of the formula (I) where $R^2$ equals COOH.

Amine (IV) can be reused for the preparation of compound (III). Alternatively, it is trapped by washing the reaction mixture with acid.

The invention is illustrated by the following examples:

EXAMPLE 1

Benzophenone hydrazone (1). A mixture of benzophenone (10 g, 54.9 mmol), hydrazine monohydrate (3.78 mL, 76.8 mmol) and absolute ethanol (20 mL) was refluxed for 12 h. The solvent was removed under reduced pressure and the crude product was recrystallized from absolute ethanol to afford 1 as white needles (8.78 g, 82%). $^1$H NMR (400 MHz, CDCl$_3$) □7.52-7.38 (m, 5H), 7.29-7.20 (m, 5H), 5.42 (br, 2H); $^{13}$C (101 MHz, CDCl$_3$)□□149.1, 138.5, 133.1, 129.5, 128.9, 128.8, 128.2, 128.1, 126.5; HRMS (ESI) calcd for $C_{13}H_{13}N_2$ [M+H]$^+$197.107, found 197.107

EXAMPLE 2

1-(Diphenylmethylene)-2-(1,1,1-trifluoropropan-2-ylidene)hydrazine (2a). A mixture of benzophenone hydrazone 1 (2 g, 10.2 mmol) and 1,1,1-trifluoroacetone (2.3 mL, 25.5 mmol) was stirred at 40° C. for 12 h. The reaction mixture was diluted in diethyl ether, dried over Na$_2$SO$_4$, filtrated and concentrated under reduced pressure to remove volatiles. The pure product 2a was obtained as a yellow oil (2.93 g, 98%). $^1$H NMR (400 MHz, CDCl$_3$)□7.69-7.63 (m, 2H), 7.47-7.33 (m, 6H), 7.21-7.13 (m, 2H), 2.08 (s, 3H); $^{13}$C (101 MHz, CDCl$_3$)□□159.8, 148.2 (q, $J_{C-F}$=34 Hz), 137.2, 134.0, 132.4, 130.5, 129.5, 128.9, 128.3, 128.1, 120.4 (q, $J_{C-F}$=276 Hz), 12.8; $^{19}$F (376 MHz, CDCl$_3$)□□□−72.3 (s, 3F); HRMS (ESI) calcd for $C_{16}H_{14}F_3N_2$ [M+H]$^+$291.111, found 291.110

EXAMPLE 3

1-(1,1-Difluoropropan-2-ylidene)-2-(diphenylmethylene)hydrazine (2b). A mixture of benzophenone hydrazone 1 (2 g, 10.2 mmol) and 1,1-difluoroacetone (2.07 mL, 25.5 mmol) was stirred at 40° C. for 12 h. The reaction mixture was diluted in diethyl ether, dried over Na$_2$SO$_4$, filtrated and concentrated under reduced pressure to remove volatiles. The pure product 2b was obtained as a yellow oil (2.59 g, 93%). $^1$H NMR (400 MHz, CDCl$_3$)□7.70-7.62 (m, 2H), 7.46-7.30 (m, 6H), 7.20-7.10 (m, 2H), 5.92 (t, 1H, J=56 Hz), 2.04 (s, 3H); $^{13}$C (101 MHz, CDCl$_3$)□□160.1, 154.5 (t, $J_{C-F}$=32 Hz), 137.4, 134.4, 132.4, 130.4, 129.3, 128.8, 128.3, 128.1, 114.4 (t, $J_{C-F}$=239 Hz), 11.0; $^{19}$F (376 MHz, CDCl$_3$)□□□−120.1 (d, 2F, J=55 Hz); HRMS (ESI) calcd for $C_{16}H_{14}F_2N_2Na$ [M+Na]$^+$295.102, found 295.102.

EXAMPLE 4

1-(1-Chloro-1,1-difluoropropan-2-ylidene)-2-(diphenylmethylene)hydrazine (2c). A mixture of benzophenone hydrazone 1 (1 g, 5.09 mmol) and 1-chloro-1,1-difluoroacetone (1.25 mL, 12.7 mmol) was stirred at 40° C. for 12 h. The reaction mixture was diluted in diethyl ether, dried over Na$_2$SO$_4$, filtrated and concentrated under reduced pressure to remove volatiles. The pure product 2c was obtained as a yellow oil (1.52 g, 97%). $^1$H NMR (400 MHz, CDCl$_{33}$) □7.83-7.76 (m, 4H), 7.62-7.54 (m, 2H), 7.51-7.44 (m, 4H), 2.03 (s, 3H); $^{13}$C (75 MHz, CDCl$_3$)□□196.75, 152.5 (t, $J_{C-F}$=28 Hz), 137.6, 132.4, 130.1, 128.3, 123.0 (t, $J_{C-F}$=289 Hz), 12.5; $^{19}$F (376 MHz, CDCl$_3$)□□□−60.1 (s, 2F); HRMS (ESI) calcd for $C_{16}H_{13}ClF_2N_2Na$ [M+Na]$^+$329.063, found 329.063

EXAMPLE 5

1-(Diphenylmethylene)-2-(3,3,4,4,4-pentafluorobutan-2-ylidene)hydrazine.

A mixture of benzophenone hydrazone 1 (1 g, 5.09 mmol) and 3,3,4,4,4-pentafluorobutan-2-one (1.6 mL, 12.7 mmol) was stirred at 40° C. for 12 h. The reaction mixture was diluted in diethyl ether, dried over Na$_2$SO$_4$, filtrated and concentrated under reduced pressure to remove volatiles. The pure product 2d was obtained as a yellow oil (1.60 g, 92%). $^1$H NMR (400 MHz, CDCl$_3$)□7.70-7.64 (m, 2H), 7.45-7.33 (m, 6H), 7.20-7.12 (m, 2H), 2.09 (s, 3H); $^{13}$C (75

MHz, CDCl$_3$) 196.7, 159.8, 148.6 (t, J$_{C-F}$=27 Hz), 137.7, 137.0, 134.1, 132.4, 130.6, 130.1, 129.4, 128.9, 128.6, 128.4, 128.0, 118.7 (qt, J$_{C-F}$=286 Hz, J$_{C-F}$=35 Hz), 110.6 (tq, J$_{C-F}$=254 Hz, J$_{C-F}$=38 Hz), 12.9; $^{19}$F (376 MHz, CDCl$_3$) −81.9 (3F), −117.5 (2F); HRMS (ESI) calcd for C$_{17}$H$_{13}$F$_5$N$_2$Na [M+Na]$^+$363.089, found 363.089

EXAMPLE 6

3,5-Bis(difluoromethyl)-1H-pyrazole

Solution of 1-(1,1-Difluoropropan-2-ylidene)-2-(diphenylmethylene)hydrazine 22 g (75 mmol) and 12 g Pyridine in 100 ml of Dichloromethane was cooled to 0° C. 19.5 g of Difluoroacetic acid anhydride was added portionwise at this temperature under intensive stirring and the mixture was finally stirred at 10° C. for 6 h. 50 ml HCl (as 5% water solurtion) were added slowly to the reaction solution to keep the temperature under 40° C. and the mixture was stirred for 5 h at 40° C. . 100 ml water and 100 ml Dichloromethane were added and organic layer was separated, washed with water, dried over MgSO$_4$ and concentrated in vacuum to give an oily product. Vacuum destillation at 92-95° C./1 mbar gave 10 g (80%) of pure 3,5-bis(difluoromethyl)-1H-pyrazole b) as a white solid with a of m.p. 70-71° C. $^1$H NMR (400 MHz, CDCl$_3$) 12.5 (br, 1H), 6.77 (t, 2H, J=54.8 Hz), 6.74 (s, 1H) ppm.

EXAMPLE 7

5-(Chlorodifluoromethyl)-3-(difluoromethyl)-1H-pyrazole, Yield 55%.

Prepared from 1-(1-Chloro-1,1-difluoropropan-2-ylidene)-2-(diphenylmethylene)hydrazine and Difluoroacetic acid anhydride.
$^1$H NMR (300 MHz, CDCl$_3$) 12.7 (br, 1H), 6.78 (s, 1H), 6.74 (t, 1H, J=54.7 Hz); $^{13}$C (75 MHz, CDCl$_3$) 145.5, 141.1, 121.3 (t, J$_{C-F}$=284 Hz), 108.5 (t, J$_{C-F}$=239 Hz), 103.2; $^{19}$F (376 MHz, CDCl$_3$) −47.6 (s, 2F), −113.7 (d, 2F, J=54.0 Hz).

EXAMPLE 8

Similar Prepared 3-(Difluoromethyl)-5-(trifluoromethyl)-1H-pyrazole, Yield 63%

NMR (400 MHz, CDCl$_3$) 12.6 (br, 1H), 6.81 (s, 1H), 6.76 (t, 1H, J=54.5 Hz); $^{13}$C (101 MHz, CDCl$_3$) 140.7, 128.8, 120.3 (q, J$_{C-F}$=266 Hz), 108.5 (t, J$_{C-F}$=237 Hz), 103.8; $^{19}$F (376 MHz, CDCl$_3$) −61.7 (s, 3F), −112.9 (d, 2F, J=54.7 Hz); HRMS (ESI) calcd for C$_5$H$_4$F$_5$N$_2$ [M+H]$^+$ 187.029, found 187.029

EXAMPLE 9

3-(Difluoromethyl)-5-(perfluoroethyl)-1H-pyrazole, Yield 58%

$^1$H NMR (300 MHz, CDCl$_3$) 12.3 (br, 1H), 6.83 (s, 1H), 6.77 (t, 1H, J=53.9 Hz); $^{13}$C (101 MHz, CDCl$_3$) 141.7, 128.3, 118.6 (qt, J$_{C-F}$=285 Hz, J$_{C-F}$=37 Hz), 109.9 (tq, J$_{C-F}$=251 Hz, J$_{C-F}$=40 Hz), 108.4 (t, J$_{C-F}$=239 Hz), 105.1; $^{19}$F (376 MHz, CDCl$_3$) −85.0 (s, 3F), −113.4 (s, 2F), −113.8 (d, 2F, J=54.7 Hz);

EXAMPLE 10

4-[(diphenylmethylene)hydrazono]-1,1,5,5-tetrafluoropent-2-en-2-ol

Solution of 1-(1,1-Difluoropropan-2-ylidene)-2-(diphenylmethylene)hydrazine 2.2 g (7.5 mmol) and 1.2 g Pyridine in 50 ml of Dichloromethane was cooled to 0° C. 19.5 g of Difluoroacetic acid anhydride was added portionwise at this temperature under intensive stirring and the mixture was finally stirred at 10° C. for 6 h. 50 ml water were added and CH$_2$Cl phase was separated and washed 2 times with water, dried over MgSO$_4$ and concentrated in vacuum to give pale yellow oil which slowly solidify.
Analytical data confirm the structure.
$^1$H NMR (400 MHz, CDCl$_3$) 12.6 (s, 1H), 7.78-7.25 (m, 10H), 7.19 (t, 1H, J=54.8 Hz), 5.91 (s, 1H), 5.70 (t, 1H, J=54.8 Hz);
$^{13}$C (101 MHz, CDCl$_3$) 187.5 (t, J$_{C-F}$=25 Hz), 156.1, 154.0 (t, J$_{C-F}$=25 Hz), 136.2, 131.3, 130.6, 130.5, 130.0, 128.5, 128.2, 128.1, 110.3 (t, J$_{C-F}$=253 Hz), 108.2 (t, J$_{C-F}$=243 Hz), 86.1; $^{19}$F (376 MHz, CDCl$_3$) −123.9 (d, 2F, J=52.6 Hz), −125.2 (d, 2F, J=54.6 Hz).

The invention claimed is:
1. A process for preparing a compound of formula (I)

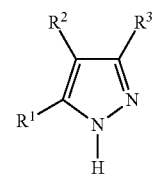

wherein:
R$^1$ and R$^3$ are each independently C$_{1-6}$-haloalkyl;
R$^2$ is selected from the group consisting of H, halogen, COOH, (C=O)OR$^5$, CN, and (C=O)NR$^6$R$^7$;
R$^5$ is selected from the group consisting of C$_{1-12}$-alkyl, C$_{3-8}$-cycloalkyl, C$_{6-18}$-aryl, C$_{7-19}$-arylalkyl, and C$_{7-19}$-alkylaryl; and
R$^6$ and R$^7$ are each independently selected from the group consisting of C$_{1-12}$-alkyl, C$_{3-8}$-cycloalkyl, C$_{6-18}$-aryl, C$_{7-19}$-arylalkyl, and C$_{7-19}$-alkylaryl; or
R$^6$ and R$^7$ are taken together with the nitrogen atom to which they are attached to form a four-, five-, or six-membered ring;
comprising reacting in step (A) a compound of formula (II)

wherein:
R$^1$ is as defined above; and
X is selected from the group consisting of F, Cl, Br, and —OC(O)R$^1$;

with a compound of formula (III)

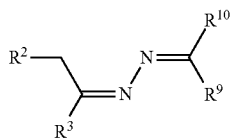

(III)

wherein:
$R^9$ and $R^{10}$ are each independently selected from the group consisting of $C_{1-12}$-alkyl, $C_{3-8}$-cycloalkyl, $C_{6-18}$-aryl, $C_{7-19}$-arylalkyl, and $C_{7-19}$-alkylaryl; and
$R^2$ and $R^3$ are as defined above;
to form a compound of formula (IV)

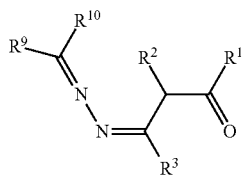

(IV)

wherein:
$R^1$, $R^2$, $R^3$, $R^5$, $R^6$, $R^7$, $R^9$, and $R^{10}$ are as defined above;
and in step (B) cyclizing the compound of formula (IV) to form the compound of formula (I).

2. The process according to claim 1, wherein:
$R^1$ and $R^3$ are each independently selected from the group consisting of difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-difluoroethyl, 2,2-dichloro-2-fluoroethyl, 2,2,2-trichloroethyl, tetrafluoroethyl ($CF_3CFH$), pentafluoroethyl, and 1,1,1-trifluoroprop-2-yl;
$R^2$ is selected from the group consisting of H, F, Cl, Br, $COOCH_3$, $COOC_2H_5$, $COOC_3H_7$, CN, $CON(CH_3)_2$, and $CON(C_2H_5)_2$;
$R^9$ is selected from the group consisting of methyl, ethyl, n-propyl, iso-propyl, n-butyl, iso-butyl, sec-butyl, t-butyl, cyclopropyl, cyclobutyl, cyclopentyl, cyclohexyl, phenyl, benzyl, phenylethyl, tolyl, 2,3-dimethylphenyl, 2,4-dimethylphenyl, 2,5-dimethylphenyl, 2,6-dimethylphenyl, 3,4-dimethylphenyl, and 3,5-dimethylphenyl;
X is selected from the group consisting of F, Cl, and —OC(O)$R^1$; and
$R^{10}$ is selected from the group consisting of $C_{1-12}$-alkyl, $C_{3-8}$-cycloalkyl, and $C_{7-19}$-arylalkyl.

3. The process according to claim 1, wherein:
$R^1$ and $R^3$ are each independently selected from the group consisting of trifluoromethyl, difluoromethyl, difluorochloromethyl, and pentafluoroethyl;
$R^2$ is selected from the group consisting of H, Cl, CN, and $COO(C_2H_5)_2$;
$R^9$ is selected from the group consisting of methyl, ethyl, n-propyl, iso-propyl, n-butyl, iso-butyl, sec-butyl, t-butyl, cyclopropyl, cyclobutyl, cyclopentyl, cyclohexyl, and benzyl;
X is selected from the group consisting of F, Cl, and —OC(O)$R^1$; and
$R^{10}$ is selected from the group consisting of $C_{1-12}$-alkyl and $C_{3-8}$-cycloalkyl.

4. The process according to claim 1, wherein:
$R^1$ and $R^3$ are each independently selected from the group consisting of $CF_2H$ and $CF_3$;
$R^2$ is selected from the group consisting of H and $COOC_2H_5$;
$R^9$ is selected from the group consisting of ethyl, n-propyl, iso-propyl, cyclopentyl, cyclohexyl, and benzyl;
X is F or —OC(O)$R^1$; and
$R^{10}$ is selected from the group consisting of methyl, ethyl, n-propyl, iso-propyl, n-butyl, iso-butyl, sec-butyl, and t-butyl.

5. The process according to claim 1, wherein:
$R^1$ and $R^3$ are each independently selected from the group consisting of $CF_2H$ and $CF_3$;
$R^2$ is H;
X is F or —OC(O)$R^1$;
$R^9$ is selected from the group consisting of iso-propyl and benzyl; and
$R^{10}$ is selected from the group consisting of methyl and ethyl.

* * * * *